United States Patent
Langbein et al.

[11] 4,085,216
[45] Apr. 18, 1978

[54] 2-(4-PHENYL-4-CYANO-N-BUTYL)-1,2,3,4-TETRAHYDRO-5(H)-PYRIDO-[4-3-b]-INDOLES AND SALTS THEREOF

[75] Inventors: Adolf Langbein, Ingelheim am Rhein; Karl-Heinz Weber, Gau-Algesheim; Adolf Bauer, Rosenheim; Karin Böke, Ingelheim am Rhein; Erich Lehr, Waldalgesheim; Franz Josef Kuhn, Bingen, Rhein, all of Germany

[73] Assignee: Boehringer Ingelheim GmbH, Ingelheim am Rhein, Germany

[21] Appl. No.: 794,937

[22] Filed: May 9, 1977

[30] Foreign Application Priority Data

May 15, 1976 Germany .............................. 2621729

[51] Int. Cl.² ..................... A61K 31/44; C07D 471/14
[52] U.S. Cl. ................. 424/263; 260/294.9; 260/296 A
[58] Field of Search ......................... 424/263 260/294.9, 296 A

[56] References Cited
U.S. PATENT DOCUMENTS 3,466,293  9/1969  Johnson et al. .................. 260/294.9

Primary Examiner—Alan L. Rotman
Attorney, Agent, or Firm—Hammond & Littell

[57] ABSTRACT

Compounds of the formula

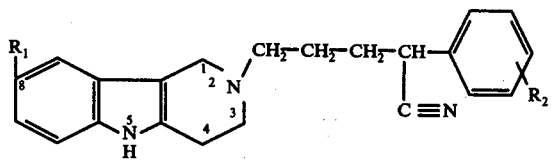

wherein
$R_1$ is hydrogen, halogen or methyl, and
$R_2$ is hydrogen, halogen, methyl or methoxy, and non-toxic, pharmacologically acceptable acid addition salts thereof; the compounds as well as their salts are useful as neuroleptics.

6 Claims, No Drawings

2-(4-PHENYL-4-CYANO-N-BUTYL)-1,2,3,4-TETRAHYDRO-5(H)-PYRIDO-[4,3-b]-INDOLES AND SALTS THEREOF

This invention relates to novel 2-(4-phenyl-2-cyano-n-butyl)-1,2,3,4-tetrahydro-5(H)-pyrido-[4,3-b]-indoles and non-toxic acid addition salts thereof, as well as to a method of preparing these compounds.

More particularly, the present invention relates to a novel class of compounds represented by the formula

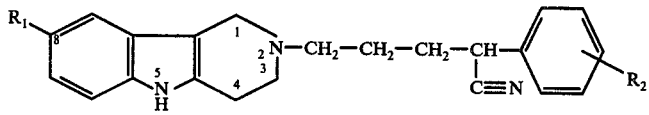

wherein,
$R_1$ is hydrogen, halogen or methyl, and
$R_2$ is hydrogen, halogen, methyl or methoxy, and non-toxic, pharmacologically acceptable acid addition salts thereof.

The compounds embraced by formula I may be prepared by reacting a pyridoindole of the formula

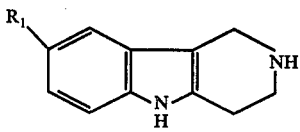

wherein $R_1$ has the same meanings as in formula I, with a halide or a reactive ester of a substituted 2-phenyl-valeronitrile of the formula

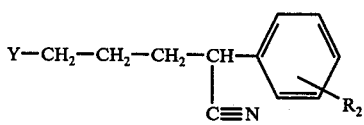

wherein
$R_2$ has the same meanings as in formula I, and
Y is a substituent which is split off during the reaction, such as halogen, arylsulfonyloxy or alkylsulfonyloxy.

The reaction is advantageously carried out in the presence of an acid-binding agent, such as triethylamine, N,N-dicyclohexyl-ethylamine, sodium carbonate, calcium carbonate, calcium oxide or, preferably, sodium bicarbonate. The 2-phenylvaleronitrile reactant of the formula III is provided in the calculated amount or in excess thereover. Although the presence of a solvent is not essential, it is more advantageous to perform the reaction in an inert organic solvent, such as chloroform, toluene, ethanol, nitromethane, tetrahydrofuran or, preferably, dimethylformamide. The reaction temperature may be varied within wide limits, but the reaction is most advantageously performed between 50° and 150° C, preferably at 100° C. The addition of catalytic or equimolar amounts of sodium iodide or potassium iodide to the reaction mixture is also of advantage.

The reaction product is isolated from the reaction mixture by means of conventional methods, and the raw products thus obtained may, if required, be purified by special methods, such as column chromatography, before they are crystallized or converted into their acid addition salts.

The compounds embraced by formula I are organic bases and therefore form addition salts with inorganic or organic acids. Examples of non-toxic, pharmacologically acceptable acid addition salts are those formed with hydrohalic acid, oxalic acid, citric acid, tartaric acid, fumaric acid, maleic acid, propionic acid, butyric acid, acetic acid, methanesulfonic acid, toluenesulfonic acid, sulfonilic acid, succinic acid, ethanephosphonic acid, 8-chlorotheophylline or the like.

The starting compounds of the formula II may be prepared by the process described in German Offenlegungsschrift No. 1,670,010.

The starting compounds of the formula III may be obtained by reacting a substituted benzyl cyanide of the formula

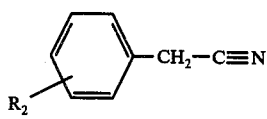

wherein $R_2$ has the same meanings as in formula I, with 1-chloro-3-bromo-n-propane. The chloride thus obtained may be converted into another halide by the Finkelstein Reaction [Berichte 43, 1528 (1910)], which can then be converted into a sulfonic acid ester of the formula III by reaction with a corresponding sulfonate.

The following are examples of compounds of the formula which may be obtained by the above-mentioned process:

2-[4-(p-Fluoro-phenyl)-4-cyano-n-butyl]-8-fluoro-1,2,3,4-tetrahydro-5(H)-pyrido[4,3-b]indole,
2-[4-(p-Fluoro-phenyl)-4-cyano-n-butyl]-8-chloro-1,2,3,4-tetrahydro-5(H)-pyrido[4,3-b]indole,
2-[4-(p-Fluoro-phenyl)-4-cyano-n-butyl]-8-bromo-1,2,3,4-tetrahydro-5(H)-pyrido[4,3-b]indole,
2-(4-phenyl-4-cyano-n-butyl)-8-fluoro-1,2,3,4-tetrahydro-5(H)-pyrido[4,3-b]indole,
2-[4-(o-Fluoro-phenyl)-4-cyano-n-butyl]-8-fluoro-1,2,3,4-tetrahydro-5(H)-pyrido[4,3-b]indole,
2-[4-(o-Bromo-phenyl)-4-cyano-n-butyl]-8-fluoro-1,2,3,4-tetrahydro-5(H)-pyrido[4,3-b]indole,
2-[4-(m-Methyl-phenyl)-4-cyano-n-butyl]-8-fluoro-1,2,3,4-tetrahydro-5(H)-pyrido[4,3-b]indole,
2-[4-(m-Methoxy-phenyl)-4-cyano-n-butyl]-8-fluoro-1,2,3,4-tetrahydro-5(H)-pyrido[4,3-b]indole,
2-[4-(p-Methoxy-phenyl)-4-cyano-n-butyl]-8-fluoro-1,2,3,4-tetrahydro-5(H)-pyrido[4,3-b]indole, and
2-[4-(p-Fluoro-phenyl)-4-cyano-n-butyl]-1,2,3,4-tetrahydro-5(H)-pyrido-[4,3-b]indole.

The following examples illustrate the present invention and will enable others skilled in the art to understand it more completely. It should be understood, however, that the invention is not limited solely to the particular examples given below.

EXAMPLE 1

2-[4-(p-Fluoro-phenyl)-4-cyano-n-butyl]-8-fluoro-1,2,3,4-tetrahydro-5(H)-pyrido[4,3-b]indole and its hydrochloride A mixture consisting of 3.8 gm (20 millimols) of 8-fluoro-1,2,3,4-tetrahydro-5(H)-pyrido[4,3-b]indole, 4.2 gm (20 millimols) of 5-chloro-2-(p-fluoro-phenyl)-valeronitrile, 2.52 gm (30 millimols) of sodium bicarbonate, 200 mgm of potassium iodide and 50 ml of dimethylformamide was stirred at 100° C until no further reaction could be detected in the thin-layer chromatogram (2 to 4 hours). The resulting suspension was evaporated at 70° C in a rotary evaporator. The residue was taken up in a mixture of 250 ml of methylene chloride and 100 ml of water. Afterwards, the organic phase was vigorously shaken five times with 100 ml of water each, dried over sodium sulfate and evaporated, leaving the reaction product as a yellowish oil which is dissolved in 15 ml of ethanol. After addition of 20 millimols of ethanolic hydrochloric acid, the acidic solution was cautiously admixed with ether until the initial turbidity just disappeared again. After some time a substance crystallized out, which was recrystallized from ethanol/ether. 6.8 gm (85.2% of theory) of the hydrochloride of the formula

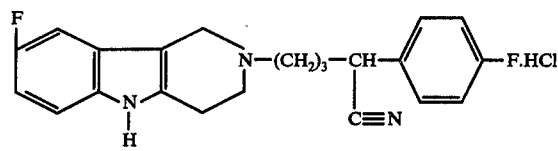

having a melting point of 235°–237° C were obtained.

Using a procedure analogous to that described in Example 1, the following compounds of the formula I and their hydrochlorides were also prepared:

| Example No. | $R_1$ | $R_2$ | Yield of hydrochloride % of theory | m.p. ° C of hydrochloride |
|---|---|---|---|---|
| 2 | 8-Cl | 4-F | 47.9 | 219 – 21 |
| 3 | 8-Br | 4-F | 34.6 | 215 – 8 |
| 4 | 8-F | H | 67.8 | 225 – 7 |
| 5 | 8-F | 2-F | 69.8 | 217 – 20 |
| 6 | 8-F | 2-Br | 67 | 237 – 9 |
| 7 | 8-F | 3-$CH_3$ | 33 | 208 – 11 |
| 8 | 8-F | 3-$OCH_3$ | 33.9 | 197 – 203 |
| 9 | 8-F | 4-$OCH_3$ | 31.4 | 191 – 5 |
| 10 | H | 4-F | 78 | 135 – 143 |
| 11 | 8-$CH_3$ | 4-F | 30 | 153 – 60 |
| 12 | 8-F | 2-$CH_3$ | 67.8 | 215 – 7 |
| 13 | 8-F | 4-$CH_3$ | 78 | 219 – 20 |
| 14 | 8-F | 2-$OCH_3$ | 62.9 | 203 – 7 |
| 15 | 8-F | 3-Cl | 57.3 | 217 – 20 |
| 16 | 8-F | 4-Cl | 55 | 234 – 7 |
| 17 | 8-F | 4-Br | 88.7 | 233 – 5 |

The compounds of the formula I and their non-toxic, pharmacologically acceptable acid addition salts have useful pharmacodynamic properties. More particularly, they exhibit an activity spectrum typical of neuroleptics in warm-blooded animals, such as mice, rats, dogs and cats, and are therefore useful as CNS-depressants, sedatives and tranquilizers.

U.S. Pat. Nos. 3,419,568, 3,448,114 and 3,466,293 disclose butyrophenone derivatives of tetrahydropyridoindoles of the formula

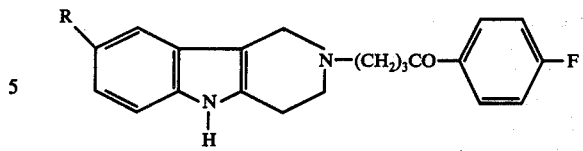

wherein R may, inter alia, be cyano, having analgesic and neuroleptic properties.

Known neuroleptics are characterized, inter alia, by their antagonistic action against adrenalin [P. A. J. Janssen et al., Arzneimittelforschung (Drug Research) 13 (1963) 205], amphetamine [J. H. Burn, R. Hobbs, Arch. inter. Pharmacodyn. 113 (1958) 290] and apomorphine in the animal test. Besides, they exhibit in behavioral tests, such as the perforated plywood test, an inhibiting effect upon the exploration drive [J. R. Borssin, P. Simin, J. M. Lwoff, Therapie 19 (1964) 571] and locomotion [P. A. J. Janssen, A. H. M. Jagenau, K. H. L. Schellekens, Psychopharmacologia 1 (1960) 389]. Finally, they also inhibit the conditioned response of small animals, for example, in the Dobrin test [P. B. Dobrin et al. Arch. inter. Pharmacodyn 178 (1969) 351].

The compounds of the present invention are superior to the known butyrophenone-substituted tetrahydropyridoindoles with respect to their neuroleptic action, and have a significantly lower toxicity. Thus, for example, 2-[4-(p-fluoro-phenyl)-4-oxo-butyl]-8-fluoro-1,2,3,4-tetrahydro-5(H)-pyrido[4,3-b]indole has an acute oral toxicity of 270 mgm/kg, whereas 2-(4-phenyl-4-cyano-butyl)-1,2,3,4-tetrahydro-5(H)-pyrido[4,3-b]indole has an $LD_{50}$ of 1400 mgm/kg p.o.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds of the present invention is from 0.0083 to 0.167 mgm/kg body weight, preferably 0.016 to 0.083 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 18

Tablets

The tablet composition is compounded from the following ingredients:

| | |
|---|---|
| 2-(4-Phenyl-4-cyano-n-butyl)-1,2,3,4-tetrahydro-5(H)-pyrido[4,3-b]indole hydrochloride | 2.0 parts |
| Lactose | 55.0 " |
| Corn starch | 38.0 " |
| Soluble starch | 4.0 " |
| Magnesium stearate | 1.0 " |
| Total | 100.0 parts |

Preparation:

The tetrahydropyridoindole compound and the magnesium stearate are intimately admixed, the mixture is granulated with an aqueous solution of the soluble starch, and the granulate is dried and intimately admixed with the lactose and the corn starch. The resulting composition is compressed into 100 mgm-tablets in a conventional tablet making machine. Each tablet contains 2 mgm of the tetrahydropyridoindole compound and is an oral dosage unit composition.

EXAMPLE 19

Coated pills

The pill core composition is compounded from the following ingredients:

| | |
|---|---|
| 2-[4-(p-Fluoro-phenyl)-4-cyano-n-butyl]-8-fluoro-1,2,3,4-tetrahydro-5(H)-pyrido[4,3-b]indole hydrochloride | 2.0 parts |
| Lactose | 28.5 " |
| Corn Starch | 17.0 " |
| Gelatin | 2.0 " |
| Magnesium stearate | 0.5 " |
| Total | 50.0 parts |

Preparation:

The tetrahydropyridoindole compound is intimately admixed with the corn starch, the mixture is moistened with an aqueous 10% solution of the gelatin, the moist mass is granulated through a 1 mm-mesh screen, and the granulate is dried at 40° C and again passed through the screen. The dry granulate is admixed with magnesium stearate, and the composition is compressed into 50 mgm-pill cores which are then coated in conventional manner with a thin shell consisting essentially of a mixture of sugar, titanium dioxide, talcum and gum arabic. The coated pills are finally polished with beeswax. Each coated pill contains 2 mgm of the tetrahydropyridoindole compound and is an oral dosage unit composition.

EXAMPLE 20

Suppositories

The suppository composition is compounded from the following ingredients:

| | |
|---|---|
| 2-(4-Phenyl-4-cyano-n-butyl)-1,2,3,4-tetrahydro-5(H)-pyrido[4,3-b]indole hydrochloride | 1.0 parts |
| Suppository base (e.g. cocoa butter) | 1699.0 " |
| Total | 1700.0 parts |

Preparation:

The tetrahydropyridoindole compound is pulverized and uniformly blended with the aid of an immersion homogenizer into the suppository base which had previously been melted and cooled to 40° C. 1700 mgm-portions of the resulting composition are poured at 35° C into cooled suppository molds and allowed to harden therein. Each suppository contains 1 mgm of the tetrahydropyridoindole compound and is a rectal dosage unit composition.

EXAMPLE 21

Hypodermic solution

The solution is compounded from the following ingredients:

| | |
|---|---|
| 2-[4-(p-Fluoro-phenyl)-4-cyano-n-butyl]-8-fluoro-1,2,3,4-tetrahydro-5(H)-pyrido[4,3-b]indole hydrochloride | 2.0 parts |

-continued

| | | |
|---|---|---|
| Sodium chloride | | 18.0 " |
| Distilled water | q.s.ad | 2000.0 " |
| | | by vol. |

Preparation:

The tetrahydropyridoindole compound and the sodium chloride are dissolved in the distilled water, the solution is filtered until free from suspended particles, and the filtrate is filled into 2 cc-ampules under aseptic conditions. The filled ampules are then sterilized and sealed. Each ampule contains 2 mgm of the tetrahydropyridoindole, and the contents thereof are an injectable dosage unit composition.

Any one of the other compounds embraced by formula I or a non-toxic, pharmacologically acceptable acid addition salt thereof may be substituted for the particular tetrahydropyridoindole compound in Examples 18 through 21. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

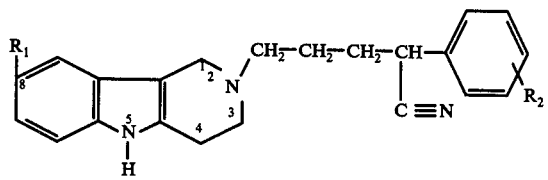

wherein
$R_1$ is hydrogen, halogen or methyl, and
$R_2$ is hydrogen, halogen, methyl or methoxy, or a non-toxic, pharmacologically acceptable acid addition salt thereof.

2. A compound of claim 1, where
$R_1$ is fluorine, and
$R_2$ is hydrogen, halogen, methyl or methoxy.

3. A compound of claim 1, which is 2-(4-phenyl-4-cyano-n-butyl)-1,2,3,4-tetrahydro-5(H)-pyrido[4,3-b]indole or a non-toxic, pharmacologically acceptable acid addition salt thereof.

4. A compound of claim 2, which is 2-[4-(p-fluorophenyl)-4-cyano-n-butyl]-8-fluoro-1,2,3,4-tetrahydro-5(H)-pyrido[4,3-b]indole or a non-toxic, pharmacologically acceptable acid addition salt thereof.

5. A neuroleptic pharmaceutical dosage unit composition consisting essentially of an inert pharmaceutical carrier and an effective neuroleptic amount of a compound of claim 1.

6. The method of depressing the central nervous system of a warm-blooded animal in need thereof, which comprises perorally, parenterally or rectally administering to said animal an effective neuroleptic amount of a compound of claim 1.

* * * * *